United States Patent
Tamerlani et al.

(10) Patent No.: US 6,891,036 B2
(45) Date of Patent: May 10, 2005

(54) PROCESS FOR THE PREPARATION OF RIBOFURANOSE DERIVATIVES

(75) Inventors: Giancarlo Tamerlani, Casola di Castel di Casio (IT); Liana Salsini, Ripa (IT); Ilaria Lombardi, Pistoia (IT); Debora Bartalucci, S. Ansano-Vinci (IT); Giovanni Cipolletti, Milan (IT)

(73) Assignee: Inalco S.p.A., Milan (IT)

( * ) Notice: Subject to any disclaimer, the term of this patent is extended or adjusted under 35 U.S.C. 154(b) by 29 days.

(21) Appl. No.: 10/447,167

(22) Filed: May 27, 2003

(65) Prior Publication Data

US 2004/0158059 A1 Aug. 12, 2004

(30) Foreign Application Priority Data

Feb. 10, 2003 (IT) ........................................ FI2003A0033

(51) Int. Cl.$^7$ ................................................. C07H 3/00

(52) U.S. Cl. ........................ 536/124; 536/4.1; 536/115; 536/119; 549/295; 549/314

(58) Field of Search .......................... 536/124, 4.1, 115, 536/119; 549/295, 314

(56) References Cited

FOREIGN PATENT DOCUMENTS

GB           1209654         10/1970      ........... C07D/99/04

OTHER PUBLICATIONS

Novak et al. "Nucleic acid components and their analogues. CXX. 2–C–methyl–D–ribose and its derivatives." Collection Czechoslov. Chem. Commun., vol. 34, pp. 857–866 (1969).*

Jenkins et al., "Branched–Chain Sugar Nucleosides", The Journal of Organic Chemistry, vol. 33, No. 6, pp. 2490–2494 Jun. (1968).

Novak et al., "Nucleic Acid Components and Their Analogues CXX. 2–C–Methyl–$_o$–Ribose and its Derivatives", Collection Czechoslov Chem. Comm., vol. 34, pp. 857–866 (1969).

* cited by examiner

Primary Examiner—James O. Wilson
Assistant Examiner—Devesh Khare
(74) Attorney, Agent, or Firm—Abelman, Frayne & Schwab

(57) ABSTRACT

The present invention relates to a new process in 3 steps starting from 2-C-methyl-D-ribopentono-1,4-lactone for the preparation of tetra-acyl ribofuranose derivatives of formula (I):

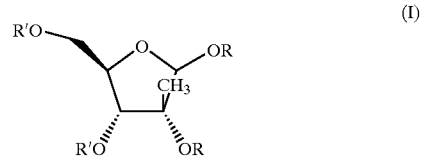

useful in the synthesis of nucleotides.

20 Claims, No Drawings

PROCESS FOR THE PREPARATION OF RIBOFURANOSE DERIVATIVES

FIELD OF THE INVENTION

The present invention relates to a process for the preparation of 1,2,3,5-tetra-O-acyl-2-C-methyl-D-ribofuranoses of formula (I) hereinafter reported, useful as intermediates in the synthesis of nucleotides.

PRIOR ART

Up to now the derivatives of 2-C-methyl-D-ribopentono-1,4-lactone and of 2-C-methyl-D-ribofuranose have been described in literature: the first group includes 2,3,5-tri-O-acetyl-2-C-methyl-D-ribopentono-1,4-lactone, 2,3,5-tri-O-benzoyl-2-C-methyl-D-ribopentono-1,4-lactone and 3,5-di-O-toluyl-2-C-methyl-D-ribopentono-1,4-lactone. These products are prepared in pyridine with a suitable acyl reagent. The drawback of this reaction is that pyridine is used in a large amount as in J. J. K. Novak et al. *Coll. Czech. Chem. Comm.* 1969, 34, 857–866.

The synthesis of the following derivatives of 2-C-methyl-D-ribofuranose is also reported in J. J. K. Novak et al. *Coll. Czech. Chem. Comm.* 1969, 34, 857–866, wherein these products are obtained by reducing 2-C-methyl-D-ribopentono-1,4-lactone with sodium borohydride or sodium amalgam:

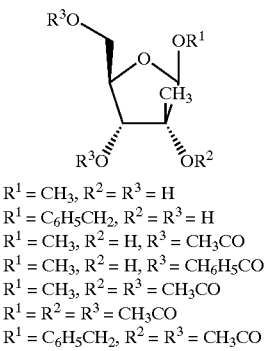

$R^1 = CH_3, R^2 = R^3 = H$
$R^1 = C_6H_5CH_2, R^2 = R^3 = H$
$R^1 = CH_3, R^2 = H, R^3 = CH_3CO$
$R^1 = CH_3, R^2 = H, R^3 = CH_6H_5CO$
$R^1 = CH_3, R^2 = R^3 = CH_3CO$
$R^1 = R^2 = R^3 = CH_3CO$
$R^1 = C_6H_5CH_2, R^2 = R^3 = CH_3CO$

In L. N. Beigelman et al., *Carb. Res.*, 1987, 166, 219–232 the synthesis of the following derivatives is reported, starting from 3-O-benzyl-1,2-O-isopropyliden-3-C-methyl-6-O-methylbenzoyl-α-D-allofuranose:

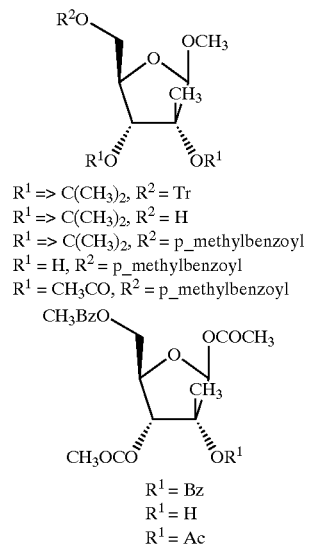

$R^1 \Rightarrow C(CH_3)_2, R^2 = Tr$
$R^1 \Rightarrow C(CH_3)_2, R^2 = H$
$R^1 \Rightarrow C(CH_3)_2, R^2 = p\_methylbenzoyl$
$R^1 = H, R^2 = p\_methylbenzoyl$
$R^1 = CH_3CO, R^2 = p\_methylbenzoyl$ $R^1 = Bz$
$R^1 = H$
$R^1 = Ac$ None of these procedures has an industrial application, that could produce in a simple and economically advantageous way the 1,2,3,5-tetra-O-acyl-2-C-methyl-D-ribofuranoses. It is also known in the art a process for the preparation of 1,2,3,5-tetra-O-benzoyl-2-C-methyl-β-D-ribofuranose, starting from 1,3,5-tri-O-benzoyl-α-D-ribofuranose of formula (V) according to the following Scheme 1:

Scheme 1

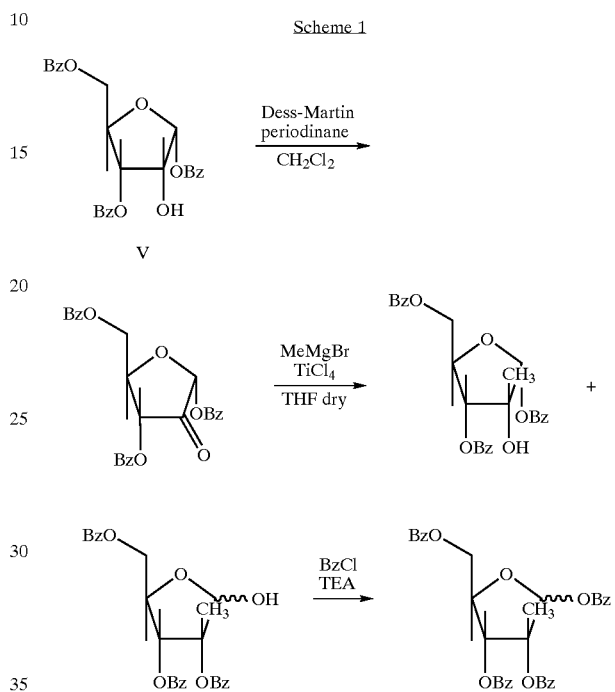

The product of formula (V) is commercially available, or it can be synthesized according to the following Scheme 2:

Scheme 2

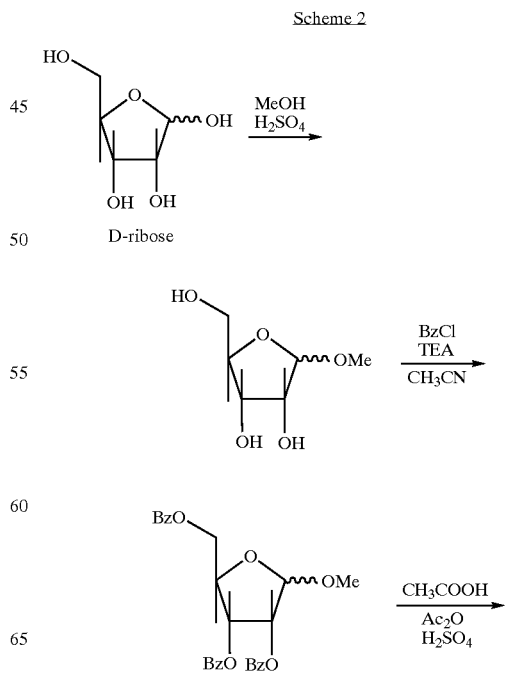

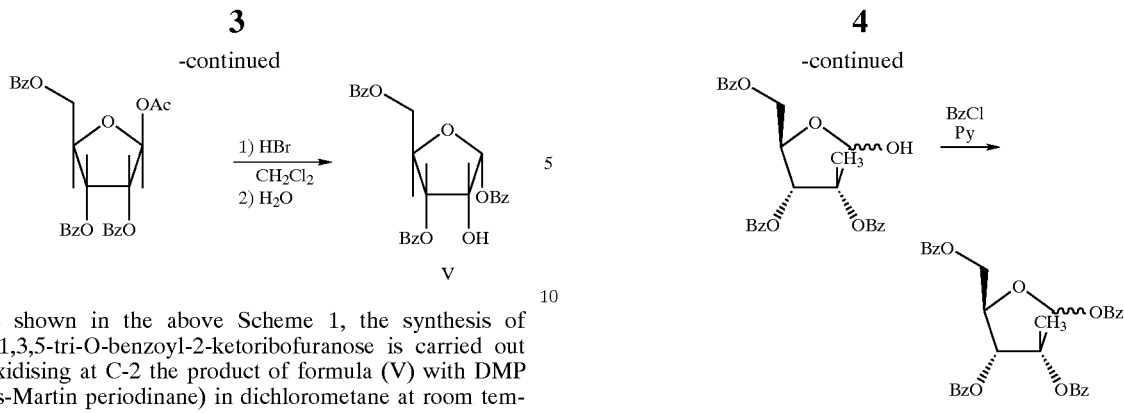

As shown in the above Scheme 1, the synthesis of α-D-1,3,5-tri-O-benzoyl-2-ketoribofuranose is carried out by oxidising at C-2 the product of formula (V) with DMP (Dess-Martin periodinane) in dichlorometane at room temperature for 12 hours. The product α-D-1,3,5-tri-O-benzoyl-2-ketoribofuranose is then recovered by crystallization from ether/hexane, (G. P. Cook et al. *Journ. Org. Chem.* 1994, 59, 4704–4706).

This reaction, as shown for example in D. B. Dess et al. *Journ. Org. Chem.* 1983, 48, 4155–4156, has several drawbacks: first of all the preparation of DMP is long and difficult (2 steps) and it cannot be easily reproduced and scaled up. Furthermore, the intermediate in this synthesis is explosive if impacted or heated at T>233° C., and the outcome of this reaction greatly depends on purity and on the physical properties of the reagent.

According to the above reported Scheme 1, α-D-1,3,5-tri-O-benzoyl-2-ketoribofuranose is reacted with MeMgBr and $TiCl_4$ in anhydrous ether at −78° C., thus obtaining 1,3,5-tri-O-benzoyl-2-C-methyl-α-D-ribofuranose. The reaction ends increasing the temperature and 1,3,5-tri-O-benzoyl-2-C-methyl-α-D-ribofuranose is purified by column chromatography. From the reaction an anomeric mixture of 2,3,5-tri-O-benzoyl-2-C-methyl-D-ribofuranoses is obtained as by-product. (M. S. Wolfe et al. *Tetrahed. Lett.* 36, 1995, 7611–7614; R. E. Harry-O'Kuru et al. *Journ. Org. Chem.* 1997, 62, 1754–1759)

This reaction has the following drawbacks: given that the reagents are not stable and must be handled with care, they have to be used in inert atmosphere taking the suitable precautions; moreover, the reaction must be carried out at a low temperature, difficult to reach in a scaled up procedure.

The subsequent synthesis of 1,2,3,5-tetra-O-benzoyl-2-C-methyl-β-D-ribofuranose is carried out starting from 1,3,5-tri-O-benzoyl-2-C-methyl-α-D-ribofuranose in dichlorometane with triethylamine and benzoyl chloride. Finally, the product 1,2,3,5-tetra-O-benzoyl-2-C-methyl-β-D-ribofuranose is crystallized from ethyl acetate and hexane. It is known in the art another process to synthesize the product 1,2,3,5-tetra-O-benzoyl-2-C-methyl-β-D-ribofuranose as shown in the following Scheme 3:

Scheme 3

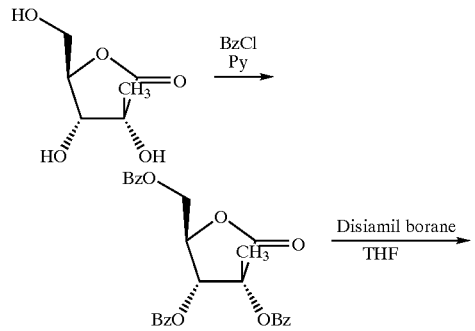

The starting product in this process, 2-C-methyl-D-ribopentono-1,4-lactone, can be prepared starting from D-fructose (R. L. Whistler et al. *Methods Carbohyd Chem.*, 2, 484, 1963), starting from 2,3-O-isopropylidene-D-glyceraldehyde (F. J. Lopez-Herrera et al. *J. Carbohyd. Chem.* 1994, 13 (5), 767–775) or from ethyl-2-C-methyl-D-ribonate (F. J. Lopez Aparicio et al. *Carbohyd. Res.*, 1984, 129, 99–109.).

The 2,3,5-tri-O-benzoyl-2-C-methyl-D-ribopentono-1,4-lactone is obtained by reacting 2-C-methyl-D-ribopentono-1,4-lactone with benzoyl chloride in pyridine for 4 hours at 65° C.–70° C.

According to S. R. Jenkins et al. *Journ. Org. Chem.* 1968, 33, 2490–2494 this reaction has the following disadvantages: as pyridine is also the solvent of the reaction it has to be used in large amount, moreover the temperature of the reaction is high.

The so obtained 2,3,5-tri-O-benzoyl-2-C-methyl-D-ribopentono-1,4-lactone is then reacted with disyamil borane (bis(3-methyl-2-butyl-borane)) in anhydrous tetrahydrofuran (THF) at room temperature for 16 hours, thus obtaining 2,3,5-tri-O-benzoyl-2-C-methyl-D-ribofuranose, that has then to be purified by column chromatography.

As reported in S. R. Jenkins et al. *J. Org. Chem.* 1968, 33, 2490–2494, the reducing agent disyamil borane is not commercially available, difficult to handle and it has to be used in inert atmosphere; moreover, the work up of this reaction is long and laborious.

Other reactions for the reduction of aldonic lactones by using as reducing agent sodium borohydride, are reported in literature. The reactions of reduction take place in acidic water at 0–3° C. In this case, the synthesis of 1,2,3,5-tetra-O-acyl-2-C-methyl-D-ribofuranoses starting from lactones obtained by this reduction, has the following disadvantages: since a mixture of pyranes and furans is obtained, they are difficult to purify, so that the yield of these reactions is low. (see for example M. L. Wolfrom et al. *Journ. Am. Chem. Soc.*, 1951, 2933–2934).

According to the above Scheme 3, 2,3,5-tri-O-benzoyl-2-C-methyl-D-ribofuranose, obtained by reduction with disyamil borane is reacted with benzoyl chloride in pyridine at 80° C. for 5 hours, thus obtaining the desired 1,2,3,5-tetra-O-benzoyl-2-C-methyl-β-D-ribofuranose.

As reported in S. R. Jenkins et al. *Journ. Org. Chem.* 1968, this reaction has some disadvantages: pyridine is also the solvent of the reaction and has to be used in large amount; moreover temperature of the reaction is high.

In view of what reported above, it is evident that a process for the preparation of tetra-acyl derivatives of 2-C-methyl-D-ribofuranose has not yet been achieved, that can be easily scaled up and does not have the disadvantages described above for the processes known in the art.

Furthermore, as far as the Applicant is acquainted, 1,2,3,5-tetra-O-acyl derivatives of 2-C-methyl-D-ribofuranose in which the acyl group in positions 1 and 2 is different from the acyl group in positions 3 and 5, have never been synthesised so far.

The interest in the preparation of these products lies in particular in their higher solubility, which is an advantageous feature in particular for the synthesis of nucleotides, wherein these products are used as intermediate.

SUMMARY

Now the Applicant has developed a new, simple and economically advantageous process for the preparation of 1,2,3,5-tetra-O-acyl-2-C-methyl-D-ribofuranoses of formula (I), which allows to overcome the disadvantages described above for the known processes.

It is therefore subject of the present invention a process for the preparation of ribofuranose derivatives of formula(I):

(I)

[Structure of formula (I): R'O-5, O, OR, CH₃, 3, 2, R'O, OR]

wherein R and R', equal or different from each other, are acyl groups chosen between C1–C6 alcanoyl groups and C7–C13 aroyl groups, optionally substituted;
comprising the following steps:
1) selective acylation in positions 3 and 5 of the lactone of formula (II) by reaction with a suitable acylating agent to obtain the 3,5-diacyl derivative of formula (III):

[Structures: (II) HO, O, O, CH₃, HO, OH → (III) R'O, O, O, CH₃, R'O, OH]

wherein R' is as described above;
2) reduction of 3,5-diacyl lactone of formula (III) coming from step 1) with a reducing agent to obtain the diacyl ribofuranose of formula (IV):

[Structures: (III) R'O, O, O, CH₃, R'O, OH → (IV) R'O, O, OH, CH₃, R'O, OH]

wherein R' is as described above;
3) acylation of 3,5-diacyl ribofuranose of formula (IV) coming from step 2) to obtain the product of formula (I)

[Structures: (IV) R'O, O, OH, CH₃, R'O, OH → (I) R'O, O, OR, CH₃, R'O, OH]

wherein R and R' are as described above,
said process being characterised in that the reduction in step 2) is carried out at pH ranging between 5 and 9 by using a borohydride of an alkaline metal as reducing agent.

Further subject of this invention are the ribofuranose derivatives of formula (I):

(I)

[Structure of formula (I): R'O-5, O, OR, CH₃, 3, 2, R'O, OR]

wherein R and R', different from each other, are acyl groups chosen between C1–C6 alcanoyl groups and C7–C13 aroyl groups optionally substituted, that are now easily obtainable by the process of the invention, and their use as intermediates in the synthesis of nucleotides.

The features and advantages of the invention will be illustrated in the following detailed description.

DETAILED DESCRIPTION OF THIS INVENTION

According to the invention, C1–C6 alcanoyl groups are, for example, formyl, acetyl and propionyl groups, and C7–C13 aroyl groups are, for example, benzoyl groups.

The above mentioned groups can optionally have one or more substituents which, for example, are selected from the group consisting of alogens, C1–C4 alkyl groups, C1–C4 alkylamino groups, C1–C4 alkyloxy groups and nitro groups.

According to the invention R and R', equal or different from each other, are preferably chosen between acetyl and benzoyl, optionally substituted with a group chosen between p-chloro and p-methyl.

The present process comprises a step 1) of selective acylation in positions 3 e 5 of 2-C-methyl-D-ribopentono-1,4-lactone of formula (II) by using a suitable acylating agent, such as an acyl chloride chosen according to the acyl group that has to be introduced in the product of formula (II). The amount of acylating agent ranges preferably between 2 and 4 equivalents with respect to the amount of the product of formula (II) that has to be acylated.

According to a particular embodiment of the present process, step 1) is carried out in presence of a base, preferably triethylamine, in an aprotic solvent selected, for example, from the group consisting of acetonitrile, acetone, ethyl acetate and dimethylformamide; preferably the reaction in step 1) is carried out in acetonitrile.

Step 1) is preferably carried out at room temperature and the reagents are added slowly so to maintain the internal temperature lower than 20° C. The reaction mixture is maintained at room temperature and TLC tests are carried out in order to check the amount of the starting material and HPLC tests are carried out in order to check the amount of the diacyl compound.

The analytical tests show the high selectivity of protection in 3 and 5 positions when the reaction is carried out in the above said conditions; indeed, the amount of tri-acyl compounds obtained is smaller than 10%.

Moreover, it is worth to note the straightforwardness of the work-up of the present step 1), in which the acylated product of formula (III) is recovered in form of an oil or a solid, by a simple precipitation with water.

The recover of the diacyl compound in form of an oil or a solid is a first purification that allows to directly crystallise the product without further steps.

Under the operative conditions of the present process, the product of formula (III) is obtained with a molar yield≧70% with respect to the starting product.

The so obtained 3,5-di-O-acyl-2-C-methyl-D-ribofuranose of formula (III) is then subjected to the reduction in step 2) in order to obtain the corresponding 3,5-di-O-acyl-2-C-methyl-D-ribofuranoside of formula (IV).

According to a preferred embodiment of the present process, the reduction in step 2) is carried out using a borohydride of an alkaline metal as a reducing agent, preferably sodium borohydride, in a mixture water/organic solvent, preferably in acetonitrile containing 2% of water, at pH ranging between 5 and 9, preferably ranging between 7 and 8.

The reaction temperature is preferably kept in a range between 0° C. and 15° C.

The reducing agent can be for example dripped in the reaction mixture in form of a 5–20% aqueous solution, wherein alkaline water is used to increase the stability of the borohydride, or the reducing reagent can be added to the reaction mixture as a solid, in portions.

The pH value can be for example maintained within the above mentioned range by dripping a mixture water:acetic acid 1:1. Under these conditions of pH, the amount of starting non-reacted product can be maintained lower than 5%, by using only 1 equivalent of reducing agent with respect to the amount of the product of formula (III) which is subjected to reduction.

Also the work-up of step 2) of the present process can be easily performed, as the product of formula (IV) can be obtained in form of an oil, by simply adding water to the reaction mixture, and it can be used in the subsequent step 3) without further purification.

Under the conditions of the present process, the molar yield of the reduction is 75% with respect to the diacyl-D-ribopentono-1,4-lactone of formula (III).

The reduction in step 2) of the present process has been analysed according to variations of pH, temperature and solvent. The reaction has a satisfactory course in a range of pH between 5 and 9, whereas some complications arise when operating out of this range of pH; the optimal course of reaction occurs at pH ranging between 7 and 8.

As shown in the following Table 1, at pH ranging between 7 and 8 the consumption of the reducing agent $NaBH_4$ is lower.

TABLE 1

| RANGE OF PH | MOLES OF $NABH_4$ (*) |
| --- | --- |
| 5 ≦ PH < 6 | 2 |
| 6 ≦ PH < 7 | 2 |
| 7 ≦ PH ≦ 8 | 1 |
| 8 < PH ≦ 9 | 1 |

(*) The necessary moles of $NaBH_4$ to complete the reaction are above reported, i.e. when the percentage of the starting product with respect to the final product is <5%. It has been noted that, when the reaction is carried out in the range of pH 5 ≦ pH < 7, a higher amountof $NaBH_4$ is necessary to reach a percentage of the starting product with respect to the final product <5%.

Moreover, when the reaction is carried out in the range of pH 8<pH≦9, the consumption of $NaBH_4$ (1 mole) is low as much as in the range of pH between 7 and 8, but a complex between the Boron and the product of formula (IV) is completely obtained.

Under these pH values, the work-up is longer than that at pH ranging between 7 and 8 because the complex has to be broken to obtain the desired product of formula (IV).

This complex, however, can be easily isolated because it crystallises in the reaction environment, and it can be re-dissolved in a mixture water/organic solvent under acid conditions for 12 hours at 70° C., for example in a mixture ethyl acetate/water acidified with acetic acid.

The reduction is not satisfactory at pH<5, because a larger amount of reducing reagent is necessary and under these conditions of pH side reactions of hydrolysis, involving acylic groups introduced in step 1), can occur.

Likewise at pH>9 the reaction proved to be inadequate, because of the high production of a further reduced by-product.

Moreover, the influence of the solvent on the reduction at step 2) was also evaluated, by performing the reaction in different mixtures solvent/water, in particular in acetonitrile/water, dimethylformamide/water, methyl acetate/water, ethyl acetate/water and dicloromethane/water. Even if the reaction successfully occurs in all these solvent mixtures, the more efficient solvents are acetonitrile and dimethylformamide, in which the completion of the reaction is reached within 30 minutes with only 1 mole of reducing agent.

As far as the temperature is concerned, the reduction reactrion according to the present process is preferably carried out at a temperature ranging between 0 and 15° C., because this range of temperatures is proved to be the best one as to the yield and purity of the reduced product of formula (IV).

Anyway, the reaction occurs also at T<0° C.; such verification was performed for example up to a temperature of −15° C. Analogously, at temperatures higher than 15° C., even if the effectiveness of the reaction decreases because of the possible formation of a further reduced product in larger amount as compared to that obtained under the optimal conditions of temperature, and the degradation of the reducing agent can increase, thus forcing to use higher amounts of the reducing agent.

Step 3) of the present process includes the acylation of 3,5-di-O-acyl-2-C-methyl-ribofuranose of formula (IV) in positions 1 and 2 with a suitable acylating agent, such as an acyl chloride, to obtain the desired final product 1,2,3,5-tetra-O-acyl-2-C-methyl-D-ribofuranose of formula (I).

The amount of acylating agent in step 3) ranges preferably between 2 and 3 equivalents in respect to the amount of the product of formula (IV) to be acylated.

According to a particular embodiment of the present process, step 3) is carried out in the presence of a base, preferably triethylamine, in an aprotic solvent selected, for example, from the group consisting of acetonitrile, acetone, ethyl acetate and dimethylformamide; preferably step 3) is carried out in acetonitrile.

Step 3) is preferably carried out at a temperature between room temperature and the temperature of reflux of the solvent, for example at a temperature ranging between 20 and 80° C.

The course of the reaction is controlled by means of HPLC tests to check the completion of the reaction.

The tetra-acylated product can be easily recovered in form of an oil or directly as a solid by dripping in the reaction mixture a volume of water equal to the volume of solvent used for the reaction, and it can be easily crystallised from alcohols.

Also the work up of step 3), perfected by the Applicant, is very fast and allows avoiding the complicated usual washings of the acylation reactions.

The molar yield of the reaction carried out under the conditions of the present process is 70% in respect of the diacyl-ribofuranose of formula (IV) obtained in step 2).

The following examples are reported to give a non-limiting illustration of the present invention.

EXAMPLE 1

Preparation of 3,5-di-O-benzoyl-2-C-methyl-D-ribopentono-1,4-lactone (product of formula (III) with R'=benzoyl group)

100 g (0.617 moles) of 2-C-methyl-D-ribopentono-1,4-lactone is added with stirring to 600 ml of acetonitrile, then 143 ml (1.23 moles) of benzoyl chloride is added in the suspension at room temperature. A mixture of 171 ml (1.23 moles) of triethylamine and 171 ml of acetonitrile is slowly (3 hours) dripped at room temperature. The reaction is stirred for 30 min. at room temperature, then an HPLC test is carried out. Thereafter 900 ml of water is added and oil is obtained. The oil is concentrated to syrup and the product crystallizes from hot toluene (490 ml). 160 g of 3,5-di-O-benzoyl-2-C-methyl-D-ribopentono-1,4-lactone is obtained as a white solid. Yield=70%. $P_f$: 110° C.

$^1$H (CDCl$_3$, 300 MHz): δ ppm 5.41 (1H, d, H-3); 4.96 (1H, ddd, H-4); 4.66 (2H, system AB, CH$_2$-5).

$^{13}$C-NMR (CDCl$_3$, 300 MHz): δ ppm 174.59 (CO-1), 78.25 (C-4); 74.38 (C-3); 72.87 (C-2); 63.03 (C-5).

EXAMPLE 2

Preparation of 3,5-di-O-toluoyl-2-C-methyl-D-ribopentono-1,4-lactone (product of formula (III) with R'=toluoyl group)

The product 3,5-di-O-toluoyl-2-C-methyl-D-ribopentono-1,4-lactone has the same synthesis as the product in example 1 by reaction of 2-C-methyl-D-ribopentono-1,4-lactone using toluoyl chloride; it is obtained by addiction of water (1.5/1 water/acetonitrile) and it crystallizes from toluene. 34 g of 3,5-di-O-toluoyl-2-C-methyl-D-ribopentono-1,4-lactone is obtained starting from 20 g of 2-C-methyl-D-ribopentono-1,4-lactone. Yield=70%. Pf: 121.5° C.

$^1$H-NMR (CDCl$_3$, 300 MHz): δ ppm 5.38 (1H, d, H-3); 4.92 (1H, m, H-4); 4.62 (2H, system AB, CH2-5).

$^{13}$C-NMR (CDCl$_3$, 300 MHz): δ ppm 174.92 (CO-1); 78.40 (C-4); 74.20 (C-3), 72.84 (C-2), 62.90 (C-5).

EXAMPLE 3

Preparation of 3,5-di-O-p-Cl-benzoyl-2-C-methyl-D-ribopentono-1,4-lactone (product of formula (III) with R'=p-chloro-benzoyl group)

The product 3,5-di-O-p-chloro-benzoyl-2-C-methyl-D-ribopentono-1,4-lactone has the same synthesis as the product in example 1 starting from 2-C-methyl-D-ribopentono-1,4-lactone, using p-chloro-benzoyl chloride; it is obtained by the addiction of water (1.5/1 water/acetonitrile) and it is used for the next reaction without further purification. Yield=72%

$^1$H-NMR (CDCl$_3$, 300 MHz): δ ppm 5.45 (1H, d, H-3); 4.92 (1-H, m, H-4); 4.62 (2H, system AB, CH2-5).

$^{13}$C-NMR (CDCl$_3$, 300 MHz): δ ppm 174.84 (CO-1); 77.88 (C-4); 74.42 (C-3); 72.66 (C-2); 63.17 (C-5).

EXAMPLE 4

Preparation of 3,5-di-O-benzoyl-2-C-methyl-D-ribopentono-1,4-lactone (product of formula (III) with R'=benzoyl group)

20 g (0.12 moles) of 2-C-methyl-D-ribopentono-1,4-lactone is added by stirring to 120 ml of acetone, then 27 ml (0.23 moles) of benzoyl chloride is added in the suspension at room temperature. A mixture of 32 ml (0.23 moles) of triethylamine and 32 ml of acetone is slowly (3 hours) dripped at room temperature cooling down to keep temperature lower then 20° C. The reaction is stirred for 30 min. at room temperature, and then an HPLC test is carried out. The salts are filtered, the solvent is evaporated and the 3,5-di-O-benzoyl-2-C-methyl-D-ribopentono-1,4-lactone crystallizes from 60 ml of toluene preheated at 50° C. 30 g of 3,5-di-O-benzoyl-2-C-methyl-D-ribopentono-1,4-lactone is obtained as a white solid. Yield=67%.

EXAMPLE 5

Preparation of 3,5-di-O-benzoyl-2-C-methyl-D-ribopentono-1,4-lactone (product of formula (III) with R'=benzoyl group)

20 g (0.12 moles) of 2-C-methyl-D-ribopentono-1,4-lactone is added by stirring to 120 ml of ethyl acetate, then 27 ml (0.23 moles) of benzoyl chloride is added in the suspension at room temperature. A mixture of 32 ml (0.23 moles) of triethylamine and 32 ml of ethyl acetate is slowly (3 hours) dripped at room temperature cooling down to keep temperature lower then 20° C. The reaction is stirred for 30 min. at room temperature, and then an HPLC test is carried out. 180 ml of demineralised water is added, the organic phase is concentrated to a syrup and 3,5-di-O-benzoyl-2-C-methyl-D-ribopentono-1,4-lactone crystallizes from 130 ml of toluene preheated at 50° C. 32 g of 3,5-di-O-benzoyl-2-C-methyl-D-ribopentono-1,4-lactone is obtained. Yield=72%.

EXAMPLE 6

Preparation of 3,5-di-O-benzoyl-2-C-methyl-D-ribofuranose (product of formula (IV) with R'=benzoyl group)

100 g (0.27 mol) of 3,5-di-O-benzoyl-2-C-methyl-D-ribopentono-1,4-lactone synthesized in Example 5 is added by stirring to a mixture of 1 l of acetonitrile and 20 ml of demineralized water. The mixture is cooled to T<15° C., then a solution of 10.2 g (0.27 moli) of sodium borohydride in 50 ml of alkaline water is dripped during an 1 hour keeping T<15° C. During the addition pH is kept between 7 and 8, by dripping a mixture of acetic acid/water 1/1. The reaction is stirred for about 30 min. at T<15° C. Then an HPLC test is carried out to estimate the amount of the starting product that is smaller than 2%. The reaction mixture is taken to pH≈5 by adding glacial acetic acid and 3 l of demineralised water is added. Oil is obtained and the aqueous layer is extracted by 2×30 ml of dichlorometane. The oil and the organic layers are mixed and they are dried over sodium sulphate anhydrous. The solvent is evaporated and the product 3,5-di-O-benzoyl-2-C-methyl-D-ribofuranose is ready for the following reaction. 80 g of oil is obtained containing 75 g, estimated through HPLC test, of product 3,5-di-O-benzoyl-2-C-methyl-D-ribofuranose as a mixture of anomers. Yield=75%.

The product 3,5-di-O-benzoyl-2-C-methyl-D-ribofuranose is used in the following reaction without further purification.

$^1$H-NMR (CDCl$_3$, 300 MHz): δ ppm 5.55 (1H, d, H-3β); 5.15 (1H, s, H-1α); 5.23 (1H, s, H-1β); 5.11 (1H, d, H-3α); 4.59 (6H, m, H-4α e H-4β; CH$_2$-5α e CH$_2$-5β).

$^{13}$C-NMR (CDCl$_3$, 300 MHz): δ ppm 103.10 (C-1β); 100.78 (C-1α); 79.84–76.52 (C-4α e C-4β; C-2α e C-2β; C-3α e C-3β); 65.79 (C-5β); 64.29 (C-5α).

EXAMPLE 7

Preparation of 3,5-di-O-benzoyl-2-C-methyl-D-ribofuranose (product of formula (IV) with R'= benzoyl group)

20 g (0.05 moles) of 3,5-di-O-benzoyl-2-C-methyl-D-ribopentono-1,4-lactone synthesized in Example 5 is added by stirring to a mixture of 200 ml of acetonitrile and 20 ml of demineralised water. The mixture is cooled to T<15° C. and 1.9 g (0.05 moles) of sodium borohydride is added in 2 portions keeping T<15° C. and pH between 7 and 8, dripping a mixture of acetic acid/demineralised water 1/1. The reaction is stirred for 30 min. at T<15° C. Then an HPLC test is carried out to estimate the amount of the starting product that is smaller than 9%. The reaction mixture is taken to pH≈5 by adding glacial acetic acid and then 600 ml of demineralised water is added. An oil is obtained and the aqueous layer is extracted by 2×15 ml of dichlorometane. The oil and the organic layers are mixed and then dried over sodium sulphate anhydrous. The solvent is evaporated and the product 3,5-di-O-benzoyl-2-C-methyl-D-ribofuranose is ready for the following reaction. 14 g of oil is obtained containing 12 g, estimated through HPLC test, of product 3,5-di-O-benzoyl-2-C-methyl-D-ribofuranose as a mixture of anomers. Yield=65%.

EXAMPLE 8

Preparation of 3,5-di-O-benzoyl-2-C-methyl-D-ribofuranose (product of formula (IV) with R'= benzoyl group)

20 g (0.05 moles) of 3,5-di-O-benzoyl-2-C-methyl-D-ribopentono-1,4-lactone synthesized in example 5 is added by stirring to a mixture of 200 ml of acetonitrile and 4 ml of demineralised water. The mixture is cooled to T<15° C. and a solution of 1.2 g (0.05 moles) of lithium borohydride in 8 ml of alkaline water is dripped in 30 min keeping T<15° C. During the addition pH is kept between 7 and 8 by dripping a mixture of acetic acid/demineralised water=1/1. The reaction is stirred for 30 min. at T<15° C. Thereafter an HPLC test is carried out to weight the amount of the starting product that is smaller than 5%. The reaction mixture is taken to pH≈5 by adding glacial acetic acid and then 600 ml l of demineralised water is added. An oil is obtained and the aqueous layer is extracted by 2×15 ml of dichlorometane. The oil and the organic layers are mixed and they are dried over sodium sulphate anhydrous. The solvent is evaporated and the product 3,5-di-O-benzoyl-2-C-methyl-D-ribofuranose is ready for the following reaction. 17 g of oil is obtained containing 15 g, estimated through HPLC test, of product 3,5-di-O-benzoyl-2-C-methyl-D-ribofuranose as a mixture of anomers. Yield=75%.

EXAMPLE 9

Preparation of the complex 3,5-di-O-benzoyl-2-C-methyl-D-ribofuranose-Boro (complex with boro of the product of formula (IV) with R'=benzoyl group)

20 g (0.05 moles) of 3,5-di-O-benzoyl-2-C-methyl-D-ribopentono-1,4-lactone synthesized in example 5 is added by stirring to a mixture of 200 ml of acetonitrile and 4 ml of demineralised water. The mixture is cooled to T<15° C. and a solution of 1.9 g (0.05 moles) of sodium borohydride in 13 ml of alkaline water is dripped in 30 min. keeping T<15° C. During the addition pH is kept between 8 and 9, dripping a mixture of acetic acid/demineralised water 1/1. During the addition a white solid is obtained which is filtered and washed with a mixture demineralised water/acetonitrile. 19 g of 3,5-di-O-benzoil-2-C-metil-D-ribofuranose are obtained. Pf: 98.4° C.

$^1$H-NMR(CDCl$_3$, 300 MHz): δ ppm 5.19 (1H, s, H-1); 5.05 (1H, d, H-3); 4.85 (1H, m, H-4); 4.63 (1H, m, CH-5); 4.06 (1H, m, CH-5).

$^{13}$C-NMR (CDCl$_3$, 300 MHz): δ ppm 107.12 (C-1); 82.07; 80.33; 77.27 (C-2,C-3,C-4); 63.09 (C-5).

EXAMPLE 10

Preparation of 3,5-di-O-benzoyl-2-C-methyl-D-ribofuranose (product of formula (IV) with R'= benzoyl group)

20 g of the complex 3,5-di-O-benzoyl-2-C-methyl-D-ribofuranose-Boro prepared as described above in Example 9 is suspended in 200 ml of ethyl acetate and 200 ml of demineralised water. The reaction mixture is acidified until pH 4.5±0.5 with acetic acid and it is refluxed 12 hours. A TLC test is carried out to check the disappearance of the starting product. The layers are separated and the organic layer is extracted with 3×100 ml of salt water. The organic layer is dried over sodium sulphate anhydrous and the solvent is evaporated. 15 g of syrup, containing 14 g of product, is obtained. The product can be used in the following step without other purification.

EXAMPLE 11

Preparation of 3,5-di-O-toluoyl-2-C-methyl-D-ribofuranose (product of formula (IV) with R'= toluoyl group)

The product 3,5-di-O-toluoyl-2-C-methyl-D-ribofuranose has the same synthesis as 3,5-di-O-benzoyl-2-C-methyl-ribofuranose in the examples 1 and 6. It is obtained as a mixture of anomers and it is used for the following reaction without further purification. Yield=75%.

$^1$H-NMR (CDCl$_3$, 300 MHz): δ ppm 5.25, 5.15 (2H, s, H-1α, H-1β); 5.09–4.32 (8H, m, H-3α, H-4α, CH$_2$-5α, H-3β, H-4β, CH$_2$-5β).

$^{13}$C-NMR (CDCl$_3$, 300 MHz): δ ppm 102.99, 100.64 (C-1β, C-1α), 79.05–76.40 (C-2α e C-2β; C-3α e C-3β; C-4α e C-4β); 64.14 (C-5α).

EXAMPLE 12

Synthesis of 3,5-di-O-p-Cl-benzoyl-2-C-methyl-D-ribofuranose (product of formula (IV) with R'=p-chloro-benzoyl group)

The product 3,5-di-O-p-Cl-benzoyl-2-C-methyl-D-ribofuranose has the same synthesis as 3,5-di-O-benzoyl-2-C-methyl-ribofuranose in the Examples 1 and 6. It crystallizes from toluene: 14 g of 3,5-di-O-p-Cl-benzoyl-2-C-methyl-D-ribofuranose is obtained starting from 20 g of 3,5-di-O-p-Cl-benzoyl-2-C-methyl-D-ribopentono-1,4-lactone. Yield=70%.

$^1$H-NMR (CDCl$_3$, 300 MHz): δ ppm 5.15 (1H, d, H-1); 5.08 (1H, d, H-3); 4.58 (3H, m, H-4, CH$_2$-5).

$^{13}$C-NMR (CDCl$_3$, 300 MHz): δ ppm 100.77 (C-1); 79.23 (C-4); 76.84 (C-3); 76.62 (C-2); 64.44 (C-5).

EXAMPLE 13

Synthesis of 1,2,3,5-tetra-O-benzoyl-2-C-methyl-β-D-ribofuranose (product of formula (I) with R=R'= benzoyl group)

100 g (0.27 moles) of 3,5-di O-benzoyl-2-C-methyl-D-ribofuranose synthesized in example 6 is added by stirring to 300 ml of acetonitrile, then 280 ml (2 moles) of triethylamine is added. 78.3 ml (0.67 moles) of benzoyl chloride is dripped at room temperature. At the end of the addition the mixture is warmed for 2 hours at 60° C., then an HPLC test is carried out.

The reaction mixture is cooled to room temperature and 150 ml of water is added. The solid is filtered, washed with a mixture acetonitrile/water=2/1 and dried under vacuum up to constant weight. 109 g of product 1,2,3,5-tetra-O-benzoyl-2-C-methyl-β-D-ribofuranose is obtained. Yield= 70%.

$^1$H-NMR (CDCl$_3$, 300 MHz): δ ppm 7.07 (1H, s, H-1); 5.96 (1H, d, H-3); 4.79 (1H, m, H-4); 4.62 (2H, system AB, CH$_2$-5).

$^{13}$C-NMR (CDCl$_3$, 300 MHz): δ ppm 97.97 (C-1); 86.82 (C-4); 78.71 (C-3); 76.3 (C-2), 64.01 (C-5).

EXAMPLE 14

Synthesis of 1,2,3,5-tetra-O-toluoyl-2-C-methyl-β-D-ribofuranose (product of formula (I) with R=R'=toluoyl group)

The product 1,2,3,5-tetra-O-toluoyl-2-C-methyl-β-D-ribofuranose has the same synthesis as the product described in Example 13 starting from 3,5-di-O-toluoyl-2-C-methyl-β-D-ribofuranose synthesized in Example 11, using toluoyl chloride. The mixture is warmed for 8 hours at 50° C., then it is cooled down to room temperature and water is dripped. The product 1,2,3,5-tetra-O-toluoyl-2-C-methyl-β-D-ribofuranose is obtained as an oil and it can be purified by column chromatography (eluent hexane/ethyl acetate: 7/3). Yield=60%.

$^1$H-NMR (CDCl$_3$, 300 MHz): δ ppm 7.05 (1H, s, H-1); 5.93 (1H, d, H-3); 4.77 (1H, m, H-4); 4.6 (2H, system AB, CH$_2$-5).

$^{13}$C-NMR (CDCl$_3$, 300 MHz): δ ppm 97.85 (C-1), 86.61 (C-4); 78.73 (C-3); 76.17 (C-2); 63.84 (C-5).

EXAMPLE 15

Synthesis of 1,2-di-O-p-Cl-benzoyl-3,5-di-O-toluoyl-2-C-methyl-α-D-ribofuranose (product of formula (I) with R'=toluoyl group), R=p-chloro-benzoyl group)

The product 1,2-di-O-p-Cl-benzoyl-3,5-di-O-toluoyl-2-C-methyl-α-D-ribofuranose has the same synthesis as the product described in example 13 starting from 3,5-di-O-toluoyl-2-C-methyl-D-ribofuranose synthesized in example 11, using p-chloro-benzoyl chloride. The mixture is warmed for 4 hours at 40° C., then it is cooled down to room temperature and water is dripped. The product 1,2-di-O-p-Cl-benzoyl-3,5-di-O-toluoyl-2-C-methyl-α-D-ribofuranose crystallizes in the reaction mixture. 18 g of 1,2-di-O-p-Cl-benzoyl-3,5-di-O-toluoyl-2-C-methyl-α-D-ribofuranose is obtained starting from 20 g of 3,5-di-O-toluoyl-2-C-methyl-D-ribofuranose. Yield=60%.

$^1$H-NMR (CDCl$_3$, 300 MHz): δ ppm 6.99 (1H, s, H-1); 5.91 (1H, d, H-3); 4.74 (2H, m, H-4, part A of a system AB, CH-5), 4.45 (1H, m, part B of a system AB, CH-5).

$^{13}$C-NMR (CDCl$_3$, 300 MHz): δ ppm 98.01 (C-1); 87.07 (C-4); 79.04 (C-3); 75.79 (C-2); 63.9 (C-5).

EXAMPLE 16

Synthesis of 1,2-di-O-benzoyl-3,5-di-O-tolyl-2-C-methyl-β-D-ribofuranose (product of formula (I) with R'=toluoyl group R=benzoyl group)

The product 1,2-di-O-benzoyl-3,5-di-O-toluoyl-2-C-methyl-β-D-ribofuranose has the same synthesis as the product in example 13 starting from 3,5-di-O-toluoyl-2-C-methyl-D-ribofuranose prepared as described in example 11, using benzoyl chloride. The reaction is warmed for 3 hours at 40° C. then it is cooled down to room temperature. The solvent is concentrated and the product 1,2-di-O-benzoyl-3,5-di-O-toluoyl-2-C-methyl-β-D-ribofuranose is purified by column chromatography (eluent hexane/ethyl acetate: 7/3).

$^1$H-NMR (CDCl$_3$, 300 MHz): δ ppm 7.07 (1H, s, H-1); 5.94 (1H, d, H-3); 4.78 (1H, ddd, H-4); 4.60 (2H, system AB, CH$_2$-5).

$^{13}$C-NMR (CDCl$_3$, 300 MHz): δ ppm 97.88 (C-1); 86.74 (C-4); 78.75 (C-3); 76.03 (C-2); 63.73 (C-5).

EXAMPLE 17

Synthesis of 1,2-di-O-acetyl-3,5-di-O-toluoyl-2-C-methyl-α-D-ribofuranose (product of formula (I) with R'=toluoyl group R=acetyl group)

The product 1,2-di-O-acetyl-3,5-di-O-toluoyl-2-C-methyl-α-D-ribofuranose has the same synthesis as the product in example 13 starting from 3,5-di-O-toluoyl-2-C-methyl-α-D-ribofuranose synthesized in example 11, using acetyl chloride. The reaction is warmed for 4 hours at 50° C. then it is cooled down to room temperature. The solvent is concentrated and the product 1,2-di-O-acetyl-3,5-di-O-toluoyl-2-C-methyl-α-D-ribofuranose is isolated by column chromatography (eluent hexane/ethyl acetate: 7/3). Yield=48%.

$^1$H-NMR (CDCl$_3$, 300 MHz): δ ppm 6.62 (1H, s, H-1); 5.67 (1H, d, H-3); 4.51 (3H, m, H-4, CH$_2$-5).

$^{13}$C-NMR (CDCl$_3$, 300 MHz): δ ppm 97.15 (C-1); 85.95 (C-4); 78.49 (C-3); 75.60 (C-2); 63.94 (C-5).

EXAMPLE 18

Synthesis of 1,2,3,5-tetra-O-p-Cl-benzoyl-2-C-methyl-α-D-ribofuranose (product of formula (I) with R'=R=p-chloro-benzoyl group)

The product 1,2,3,5-tetra-O-p-Cl-benzoyl-2-C-methyl-α-D-ribofuranose has the same synthesis as in example 13 starting from 3,5-di-O-p-chloro-benzoyl-2-C-methyl-D-ribofuranose prepared as in example 12, using p-chloro-benzoyl chloride. 1,2,3,5-tetra-O-benzoyl-2-C-methyl-β-D-ribofuranose. The mixture is kept for 12 hours at room temperature. The product 1,2,3,5-tetra-O-p-Cl-benzoyl-2-C-methyl-α-D-ribofuranose is obtained adding water to the reaction mixture same volume of acetonitrile. The product crystallizes from ethanol. 21.6 g of 1,2,3,5-tetra-O-p-Cl-benzoyl-2-C-methyl-α-D-ribofuranose is obtained starting from 20 g of 3,5-di-O-p-Cl-benzoyl-2-C-methyl-D-ribofuranose Yield 75%.

$^1$H-NMR (CDCl$_3$, 300 MHz): δ ppm 6.96 (1H, s, H-1); 5.86 (1H, d, H-3); 4.74 (2H, m, H-4 e part A of a system AB); 4.48 (1H, m, part B of a system AB).

$^{13}$C-NMR (CDCl$_3$, 300 MHz): δ ppm 98.10 (C-1); 86.92 (C-4); 78.78 (C-3); 76.32 (C-2); 63.74 (C-5).

EXAMPLE 19

Synthesis of 1,2-di-O-benzoyl-3,5-di-O-p-Cl-benzoyl-2-C-methyl-D-ribofuranose (product of formula (I) with R=benzoyl group, R'=p-chloro-benzoyl group)

The product 1,2-di-O-benzoyl-3,5-di-O-p-Cl-benzoyl-2-C-methyl-D-ribofuranose has the same synthesis as the product in example 13 starting from 3,5-di-O-p-Cl-benzoyl-2-C-methyl-D-ribofuranose synthesized in example 12, using benzoyl chloride.

The product 1,2-di-O-benzoyl-3,5-di-O-p-Cl-benzoyl-2-C-methyl-D-ribofuranose crystallizes from ethanol. 18.7 g of 1,2-di-O-benzoyl-3,5-di-O-p-Cl-benzoyl-2-C-methyl-D-ribofuranose is obtained starting from 20 g of 3,5-di-O-p-Cl-benzoyl-2-C-methyl-D-ribofuranose. Yield=72%.

$^1$H-NMR (CDCl$_3$, 300 MHz): δ ppm 7.01 (1H, s, H-1); 5.89 (1H, d, H-3); 4.73 (2H, m, H-4 e part A of a system AB); 4.51 (1H, m, part B of a system AB).

$^{13}$C-NMR (CDCl$_3$, 300 MHz): δ ppm 98.02 (C-1); 86.72 (C-4); 78.67 (C-3); 76.38 (C-2); 63.78 (C-5).

EXAMPLE 20

Sythesis of 1,2-di-O-toluoyl-3,5-di-O-p-Cl-benzoyl-2-C-methyl-D-ribofuranose (product of formula (I) with R=toluoyl group, R'=p-chloro-benzoyl group)

The product 1,2-di-O-toluoyl-3,5-di-O-p-Cl-benzoyl-2-C-methyl-D-ribofuranose has the same synthesis as the product in example 13 starting from 3,5-di-O-p-Cl-benzoyl-2-C-methyl-D-ribofuranose synthesized in example 12, using toluoyl chloride.

The product 1,2-di-O-toluoyl-3,5-di-O-p-Cl-benzoyl-2-C-methyl-D-ribofuranose crystallizes adding water to the reaction mixture same volume of acetonitrile. 23.7 g of 1,2-di-O-toluoyl-3,5-di-O-p-Cl-benzoyl-2-C-methyl-D-ribofuranose is obtained from 20 g of 3,5-di-O-p-Cl-benzoyl-2-C-methyl-D-ribofuranose. Yield=83%.

$^1$H-NMR (CDCl$_3$, 300 MHz): δ ppm 6.97 (1H, s, H-1); 5.88 (1H, d, H-3); 4.72 (2H, m, H-4 e part A of a system AB); 4.49 (1H, m, part B of a system AB).

$^{13}$C-NMR (CDCl$_3$, 300 MHz): δ ppm 97.87 (C-1); 86.54 (C-4); 78.64 (C-3); 76.29 (C-2); 63.54 (C-5).

EXAMPLE 21

Synthesis of 1,2-di-O-acetyl-3,5-di-O-p-Cl-benzoyl-2-C-methyl-α-D-ribofuranose (product of formula (I) with R=acetyl group, R'=p-chloro-benzoyl group)

The product 1,2-di-O-acetyl-3,5-di-O-p-Cl-benzoyl-2-C-methyl-α-D-ribofuranose has the same synthesis as the product in the example 13 starting from 3,5-di-O-p-Cl-benzoyl-2-C-methyl-α-D-ribofuranose synthesized in example 12, using acetyl chloride. The product 1,2-di-O-acetyl-3,5-di-O-p-Cl-benzoyl-2-C-methyl-α-D-ribofuranose is purified by column chromatography (eluent hexane/ethyl acetate: 7/3).

$^1$H-NMR (CDCl$_3$, 300 MHz): δ ppm 6.60 (1H, s, H-1); 5.62 (1H, d, H-3); 4.58 (2H, m, H-4 e part A of a system AB); 4.43 (1H, dd, part B of a system AB).

$^{13}$C-NMR (CDCl$_3$, 300 MHz): δ ppm 97.15 (C-1); 85.80 (C-4); 78.16 (C-3); 76.12 (C-2); 64.44 (C-5).

EXAMPLE 22

Synthesis of 3,5-di-O-benzoyl-2-C-methyl-D-ribopentono-1,4-lactone (product of formula (III) with R'=benzoyl group)

13.2 Kg of acetonitrile are introduced into a 100 l reactor while stirring. 2.8 Kg (17.3 moles) of 2-C-methyl-D-ribopentono-1,4-lactone and 4.76 Kg (33.8 moles) of benzoyl chloride are added. In another reactor a solution made up by diluting 3.43 Kg (33.9 moles) of triethylamine and 3.71 Kg of acetonitrile is prepared. This solution is dripped in the 100 l reactor during 3 hours keeping the temperature at 20° C.±2° C. After 30 min. from the end of the addition an HPLC test is carried out to estimate the amount of the starting material that is smaller than 1% compared to 3,5-di-O-benzoyl-2-C-methyl-D-ribopentono-1,4-lactone and the amount of 2,3,5-tri-O-benzoyl-2-C-methyl-D-ribopentono-1,4-lactone is smaller than 10%. Afterward 25 l of demineralised water is introduced into the reactor, the stirring is stopped and the layers are separated. After 5 min. stirring and 1 hour at rest, the layers are separated: the organic (weight 12.9 Kg) is transferred in a 25 l glass reactor and then washed with 10 l of demineralised water. The layers are separated: the organic phase is put away, and the aqueous phase is put together with the aqueous layer of the first extraction and they are washed with 1.5 l of toluene. The stirring water layer is eliminated, the organic layer is mixed to the organic phase of the first extraction. The organic layer is concentrated to syrup under vacuum at T<50° C. In another reactor 14.5 Kg of toluene is heated at 50° C. and then it is added to the syrup. The mixture is stirred 1 hour then it is cooled at 20° C. It is filtered and the panel is washed with 3 Kg of toluene and with 2.1 Kg of hexane. 4.6 Kg of 3,5-di-O-benzoyl-2-C-methyl-D-ribopentono-1,4-lactone is obtained. Yield=72%.

EXAMPLE 23

Synthesis of 3,5-di-O-benzoyl-2-C-methyl-D-ribofuranose (product of formula (IV) with R'=benzoyl group)

96.7 Kg of acetonitrile and 2.4 l of demineralised water is introduced into a 500 l reactor. Then 11 Kg (29.7 moles) of 3,5-di-O-benzoyl-2-C-methyl-D-ribopentono-1,4-lactone synthesized in example 22, is added and the reactor is cooled down to 3° C. In another reactor a solution of 1.12 Kg (29.7 moles) of sodium borohydride in 7.2 l of alkaline water is prepared and cooled down to 5° C. This solution is dripped in the 500 l reactor during 6 hours under stirring at pH 7.5±0.5 and at a temperature of 3° C.±2° C. This range of pH is kept by dripping acetic acid at 50%. After 10 min. from the end of the addition an HPLC test is carried out to estimate the amount of the starting material that is smaller than 2% and the further reduced products are negligible. 11 l of acetic acid is dripped with care in the reaction and then 314 l of demineralised water is added. The stirring is stopped for 2 hours. An oil is separated and then the layer water/acetonitrile is washed with 2×2.6 Kg of dichlorometane. The organic washings are mixed to the oil and they are concentrated up to syrup (8.8 Kg) that is used in the following reaction without further purification.

EXAMPLE 24

Synthesis of 1,2,3,5-tetra-O-benzoyl-2-C-methyl-β-D-ribofuranose (product of formula (I) with R=R'=benzoyl group)

The product 3,5-di-O-benzoyl-2-C-methyl-D-ribofuranose (8.25 Kg ~22.2 moles) synthesized in example 23 is dissolved in 21 Kg of acetonitrile and then loaded in a 100 l reactor. 16.8 Kg (166.5 moles) of triethylamine is added and 9.8 Kg (69.7 moles) of benzoyl chloride is dripped; the temperature grows spontaneously. Then the mixture is heated at 60° C. for 4 hours. Thereafter the reaction is cooled at room temperature and 13.7 l of water is dripped. The mixture is cooled at 0° C. and is kept under stirring 1 hour. The solid is filtered and washed with 8 l of a mixture 2/1 acetonitrile/water cooled at 0° C. and then with 4.7 Kg of cold methyl alcohol.

9.65 Kg of 1,2,3,5-tetra-O-benzoyl-2-C-methyl-β-D-ribofuranose is obtained. Yield=76%

EXAMPLE 25

Synthesis of 3,5-di-O-benzoyl-2-C-methyl-D-ribopentono-1,4-lactone (product of formula (III) with R'=benzoyl group)

37.8 Kg of ethyl acetate is introduced in a 200 l reactor and then placed under stirring. 7 Kg (43.2 moles) of 2-C-methyl-D-ribopentono-1,4-lactone and 11.75 Kg (83.6 moles) of benzoyl chloride are added. In another reactor a solution obtained by diluting 8.5 Kg (83.6 moles) of triethylamine in 10.5 Kg of ethyl acetate is prepared. 200 l of this solution is added in the 200 l reactor during 3 hours keeping the temperature at 20° C.±2° C. After 30 min. from the end of the addition an HPLC test is carried out to estimate the amount of the starting material that is smaller than 1% compared to 3,5-di-O-benzoyl-2-C-methyl-D-ribopentono-1,4-lactone. 63 l of demineralised water is added in the reactor, the stirring is stopped and the layers are separated. The aqueous layer is eliminated and the organic phase, is concentrated to syrup. In another reactor 40 Kg of toluene is heated at 50° C. and then added to the syrup. The mixture is stirred for 1 hour then slowly cooled down to 20° C. It is filtered under vacuum and the panel is washed with 10.38 Kg of toluene and with 6 Kg of hexane. 11.2 Kg of 3,5-di-O-benzoyl-2-C-methyl-D-ribopentono-1,4-lactone is obtained. Yield=70%.

What is claimed is:

1. A process for the preparation of ribofuranose derivatives of formula (I):

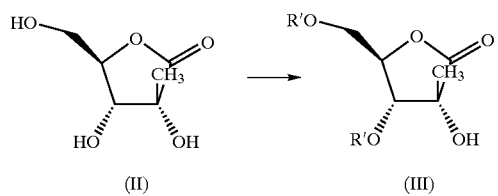

wherein R and R', equal or different from each other, are acyl groups chosen between C1–C6 alcanoyl groups and C7–C13 aroyl groups, optionally substituted with one or more substituents selected from the group consisting of alogens, alkyl groups C1–C4, alkylamino groups C1–C4, alkylocy groups C1–C4 and nitro groups; comprising the following steps:

1) selective acylation in positions 3 and 5 of the lactone of formula (II) by reaction with an acyl chloride R'Cl selected according to the acyl group that has to be introduced in the product of formula (II) to abtain the 3,5-diacyl derivative of formula (III):

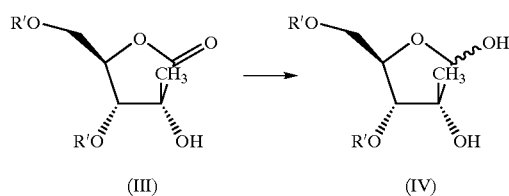

wherein R' is as described above;

2) reduction of 3,5-diacyl lactone of formula (III) with a

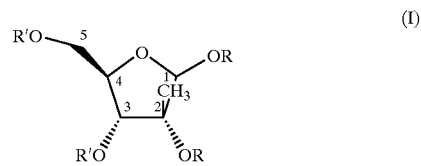

wherein R' is as described above;

3) acylation of 3,5-diacyl ribofuranose of formula (IV) to obtain the product of formula (I)

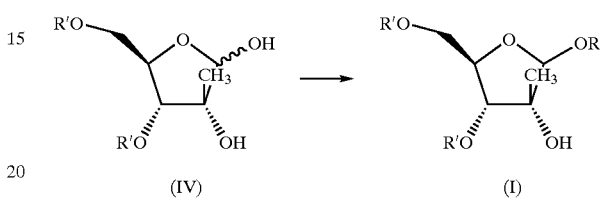

wherein R and R' are as described above, said process being characterised in that the reduction in step 2) is carried out at pH ranging between 5 and 9 by using a borohydride of an alkaline metal as reducing agent.

2. Process according to claim 1, in which the said reducing agent in step 2) is sodium borohydride.

3. Process according to claim 1, in which the said reduction in step 2) is carried out at pH ranging between 7 and 8.

4. Process according to claim 1, in which the said reduction in step 2) is carried out at pH ranging between 8 and 9, and yields a complex between Boron and the product of formula (IV), from which the product (IV) is obtained by dissolving the complex in a mixture water/organic solvent under acid conditions.

5. Process according to claim 1, in which the said reduction in step 2) is carried out at a temperature ranging between 0° C. and 15° C.

6. Process according to claim 1, in which the said reduction in step 2) is carried out in a mixture water/organic solvent in which the organic solvent is selected from the group consisting of acetonitrile, dimethylformamide, methyl acetate, ethyl acetate and dichlorometane.

7. Process according to claim 6, in which the said reduction in step 2) is carried out in a mixture water/organic solvent in which the organic solvent is chosen between acetonitrile and dimethylformamide.

8. Process according to claim 1, in which the said reduction in step 2) is carried out with sodium borohydride in an amount comprised between 0.5 and 2 equivalents with respect to the product of formula (III), in acetonitrile containing 2% of water, at pH ranging between 7 and 8, and at temperature ranging between 0° C. and 5° C.

9. Process according to claim 1, in which the said acylation in steps 1) and 3) is carried out in an aprotic solvent in the presence of a base.

10. Process according to claim 9, in which the said aprotic solvent is selected from the group consisting of acetonitrile, acetone, ethyl acetate, dimethylformamide and the said base is triethylamine.

11. Process according to claim 10, in which said aprotic solvent is acetonitrile.

12. Process according to claim 1, in which the said acylation in step 1) is carried out at room temperature.

13. Process according to claim 1, in which the said acylation in step 1) is carried out at room temperature with an amount of acylating of said acyl chloride comprised between 2 and 4 equivalents with respect to the product of formula (II).

14. Process according to claim 1, in which the said acylation in step 3) is carried out at a temperature ranging between 20° C. and 80° C. with an amount said acyl chloride comprised between 2 and 3 equivalents with respect to the amount of product of formula (IV).

15. Process according to claim 1, in which R and R', equal or different from each other, are chosen between acetyl and benzoyl, optionally substituted with a group chosen between p-chloro and p-methyl.

16. Ribofuranose derivatives of formula (I)

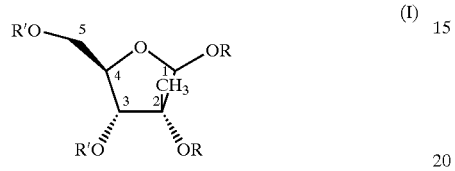

(I)

wherein R and R', different from each other, are acyl groups chosen between C1–C6 alcanoyl groups and C7–C13 aroyl groups, optionally with one or more substituents selected from the group consisting of alogens, alkyl groups C1–C4, alkylamino groups C1–C4, alkyloxy groups C1–C4 and nitro groups.

17. Ribofuranose derivatives according to claim 16, in which the said alcanoyl group C1–C6 is selected from the group consisting of formyl, acetyl and propionyl, and said aroyl group C7–C13 is benzoyl, optionally substituted with one or more substituents selected from the group consisting of alogens, alkyl groups C1–C4, alkylamino groups C1–C4, alkyloxy groups C1–C4, and nitro groups.

18. Ribofuranose derivatives according to claim 16, selected from the following products:

1,2-di-O-p-chloro-benzoyl-3,5-di-O-toluoyl-2-C-methyl-a-D-ribofuranose;

1,2-di-O-benzoyl-3,5-di-O-toluoyl-2-C-methyl-b-D-ribofuranose;

1,2-di-O-acetyl-3,5-di-O-toluoyl-2-C-methyl-a-D-ribofuranose;

1,2-di-O-benzoyl-3,5-di-O-p-chloro-benzoyl-2-C-methyl-D-ribofuranose;

1,2-di-O-toluoyl-3,5-di-O-p-chloro-benzoyl-2-C-methyl-D-ribofuranose; and 1,2-di-O-acetyl-3,5-di-O-p-chloro-benzoyl-2-C-methyl-a-D-ribofuranose.

19. Boron complex of the product of formula (IV) 3,5-di-O-benzoyl-2-C-methyl-D-ribofuranose whose $^{13}$C-NMR (CDCl$_3$, 300 MHz) spectrum has the following main peaks: δ ppm 107.12 (C-1), 82.07; 80.33; 77.27 (C-2, C-3, C-4), 63.09 (C-5).

20. Ribofuranose derivatives of formula (IV), selected from the following products:

3,5-di-O-benzoyl-2-C-methyl-D-ribofuranose;

3,5-di-O-toluoyl-2-C-methyl-D-ribofuranose; and 3,5-di-O-p-chloro-benzoyl-2-C-methyl-D-ribofuranose.

* * * * *